Figure 1:
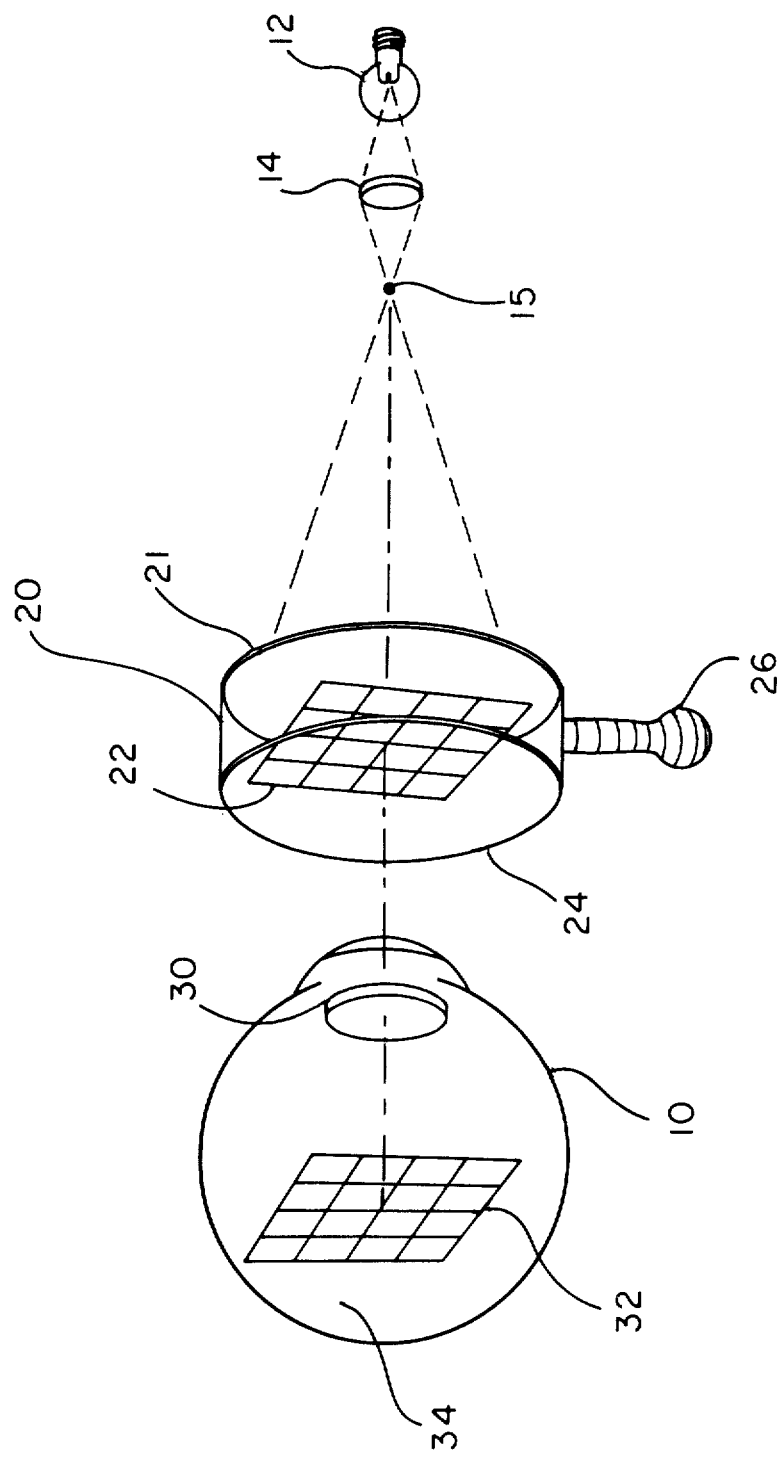

United States Patent [19]

Howland

[11] 3,947,186

[45] Mar. 30, 1976

[54] EYE-TEST LENS AND METHOD

[76] Inventor: Bradford Howland, 77 Massachusetts Ave., Cambridge, Mass. 02139

[22] Filed: Mar. 17, 1975

[21] Appl. No.: 558,825

[52] U.S. Cl. .................. 351/17; 350/190; 351/34; 351/39
[51] Int. Cl.² ...................... A61B 3/02; G02B 3/06
[58] Field of Search ............ 351/17, 19, 22, 39, 34, 351/28, 29; 356/126; 350/190

[56] References Cited
UNITED STATES PATENTS
3,574,464   4/1971   Howland ..................... 350/190 X

*Primary Examiner*—Paul A. Sacher
*Attorney, Agent, or Firm*—Jack Larsen

[57] ABSTRACT

The invention is a test lens made to fit a standard optometrist's trial-lens frame. The lens is a crossed-cylinder astigmator of about ± 5 diopter strength, preferably formed by cementing together a first plano-convex cylinder lens of about 5 diopter strength and a second equal-strength plano-concave cylinder lens with a parallelogram grid sandwiched between them, the grid lines being about one millimeter apart in each of the parallel sets, and inclined one set to the other at an angle of about 73 degrees, the axes of principal curvature of the lens elements being perpendicular one to the other, and respectively parallel one to each of the diagonals of the grid elements. The subject under test views monocularly a spectrally pure point source through the test lens. Ideally, he sees an undistorted pattern of vertical and horizontal lines; but depending on the nature of his refractive defect, various distortions of the grid pattern are seen which the subject may then sketch, or identify, with the aid of an atlas of variously distorted patterns.

10 Claims, 6 Drawing Figures

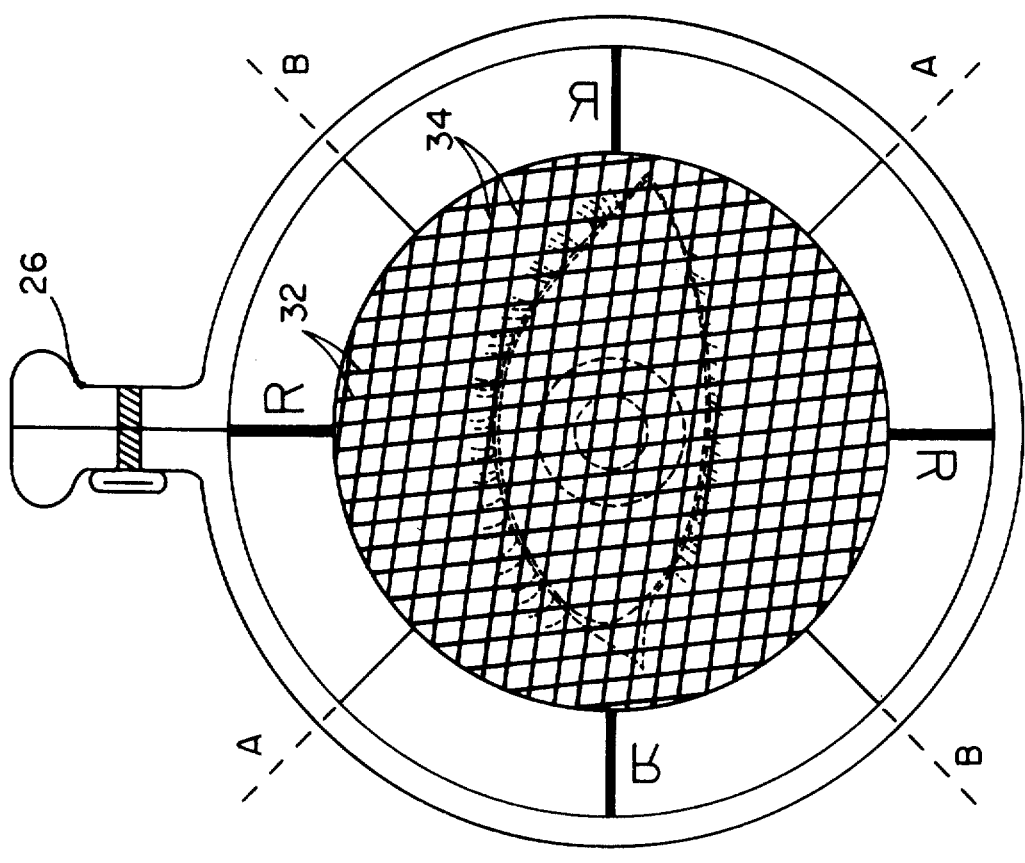
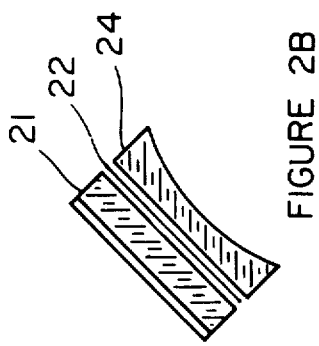
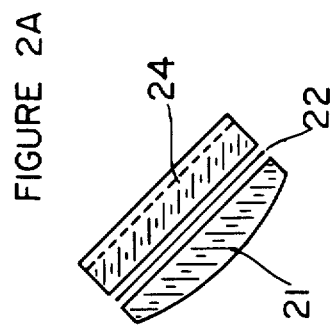
FIGURE 2
FIGURE 2A
FIGURE 2B

EYE-TEST LENS AND METHOD

This invention relates to Ophthalmology, and particularly to a novel test lens for study of monochromatic aberrations of the eye. The present invention has resulted from the extension of the methods and apparatus described in my U.S. Pat. No. 3,574,464 granted Apr. 13, 1971 for the testing of camera lenses to the test of the human eye. The optical theory upon which the present invention rests is explained in the patent in connection with FIGS. 10 and 11 thereof.

FIG. 10 of the patent illustrates a test of a camera lens in which, as disclosed in the specification, a photograph is taken of a point source of light through a weak, crossed-cylinder lens and an orthogonal grid pattern. It is demonstrated in the patent that the extent and character of certain errors in camera focus are measured by the amount of apparatus rotations and stretchings of the elements of the grid pattern as they appear on the film. The patent also discloses that various types of aberrations may be detected in the observed distortions of the shadow image of the grid as it appears on the film. The patent contemplates that the crossed-cylinder lenses used for the test have only a weak power consistent with the minor errors in any practical camera lens.

I have found that use of a relatively strong crossed-cylinder lens and a grid pattern to view a point source provides a powerful method to determine aberrations of the human eye more complex than myopia and astigmatism such as, for example, occur in the pathological condition known as "conical cornea."

Since the new method requires an untrained person to make subjective observations and report on them, and since the testing is normally done by an ophthalmic physician or technician, the apparatus is made compatible with the commonly used optometrist's trial-lens frame.

The use of a special test lens and grid pattern for the detection of monochromatic aberrations of the eye was treated in Volume I of Helmholtz's "Treatise on Physiological Optics." In the third German edition of the Treatise, as edited by Gullstrand, an apparatus is described which is termed "Tscherning's aberroscope" on page 437. "The instrument consists of two systems of perpendicular opaque lines ruled on the flat side of a planoconvex lens, which is held in front of the eye, from 10 to 20 cm away, and toward a luminous point. The shadows of the lines are seen in the blur circle produced by the artificial myopia." Gullstrand, in his commentary which follows this brief description of the aberroscope, is highly critical of the theory and effectiveness of the instument. One problem with the aberroscope is that the eye struggles to overcome the artificial myopia by its accommodation. The present invention avoids this, because it operates on the principle of inducing an artificial astigmatism which cannot be reduced by accommodation.

At page 440 Gullstrand mentions Helmholtz' famous dictum, that the monochromatic aberrations of the eye are such as would not be tolerated in any good optical instrument. Possibly for this reason we were slow to recognize that the same general principal which provided a very sensitive test for extremely slight defects in camera lenses, as described in the above-mentioned patent, could also be adapted with a much stronger crossed-cylinder lens to detect the much more severe aberrations, particularly asymmetrical aberrations which may occur in the eye. Or possibly the disparaging nature of Gullstrand's remarks about Tscherning's work turned aside research that may have resulted in the present discovery.

I have found that by using an artificial astigmatism in connection with a grid pattern instead of the artificial myopia described by Tscherning, a sensitive test results that is mathematically manageable. As pointed out by Gullstrand, the separation of the grid from the lens complicates the mathematics. Troublesome as this may have been to Gullstrand, in the case of the crossed-cylinder method this is seen to be corrected by a simple linear transformation which may be called an "italic" transformation in that it changes common type to italics, or vice versa.

It is, accordingly, a feature of the present invention to provide an improved test lens with an associated parallelogram grid which is transformed to a square shadow pattern at the cornea and then transformed by a normal eye to a square blur pattern at the retina. It is a further feature of the present invention to provide an improved test using the novel test lens.

Figure 3A:
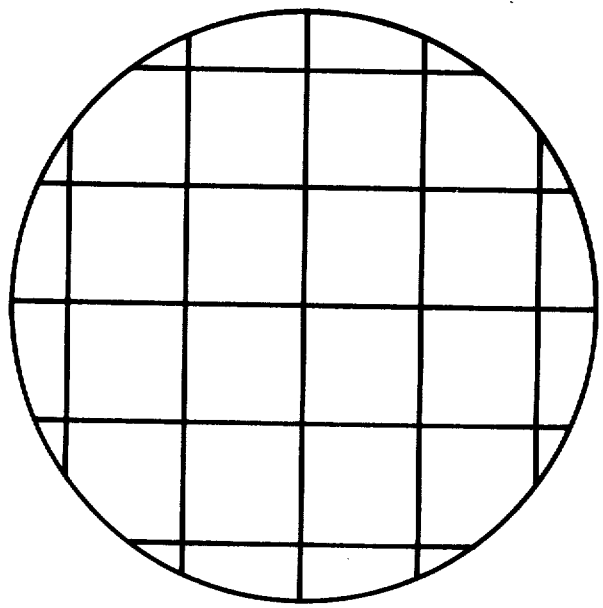
Figure 3B:
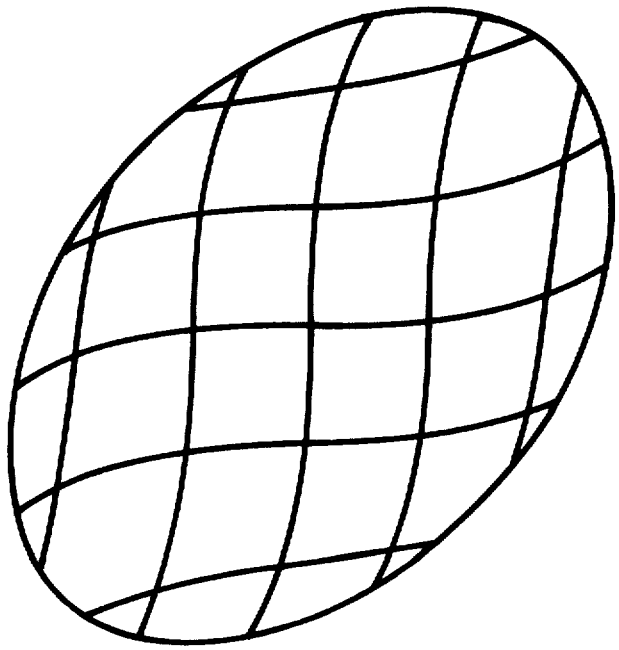

Other features and objects of the invention will, in part, be obvious and in part be apprehended from the following specification taken in connection with the accompanying drawings of which:

FIG. 1 is a schematic illustration of the relation of the test apparatus and the eye under test, FIG. 2 is a plan view of the parallelogram grid and indexing marks of the test lens, FIG. 2A is an exaggerated section through the lens along line AA, and FIG. 2B is an exaggerated section along the line BB, FIG. 3A is the perceived image by a normal eye, and FIG. 3B is the perceived image by an eye with spherical aberration.

FIG. 1 illustrates the test arrangement. The subject eye 10 views light from a source 12, which is condensed by a lens 14 (such as a microscope objective) to form a virtual point source 15 of light. The light passes through the test lens assembly 20 comprising a positive cylinder lens 21, a grid 22, and a negative cylinder lens 24, all retained by a ring 25 with a handle 26, then continues through the lens 30 of the eye to form an image 32 on the retina 34. In practice the assembly 20 is proportioned to fit a standard test frame, and therefore, is positioned approximately three centimeters in front of the cornea, the special lens being inserted in the outermost slot in the trial frame. With the test lens in this position the grid line sets, which intersect at an angle of 73°, transform to a substantially square pattern at the cornea and are viewed as a square grid pattern by the normal eye.

FIG. 2 is a plan view of the test lens viewed facing the subject eye. Since the lens is used in a low ambient light condition, it is desireable to have the grid marked for orientation in assembly and in use. The grid lines 32 spaced approximately 1.25 millimeters apart are inclined 8½° from the vertical, which is by the line R ⅄ . The grid lines 34, also spaced apart by approximately 1.25 millimeters, are inclined 8.5° from the horizontal indicated by the line marked ⊼ ⊻ on the reticle. The sets of lines 32 and 34 are seen to intersect at the acute angle of 73°. The lines AA and BB are principle diameters bisecting respectively the acute and obtuse angles between the grid sets. The positive cylinder lens 21 is oriented with its principle axis along BB, and, as shown in FIG. 2A, its plane of greatest curvature is in the section through the line AA. The negative cylinder lens 24 on the other side of the grid 22 is oriented with its principle axis parallel to the line AA, and as shown in FIG. 2B, its plane of greatest curvature is in the section through the line BB . . . . It will be apparent that if the lens is situated so that the symbol R at the top appears normal, looking towards the subject, the orientation is proper whether the lens 21 or the lens 24 be the outermost element of the test lens as inserted in the frame.

The actual preferred angle of intersection of the grid sets to transform into a square pattern of the cornea of the eye depends upon the desired strength of the crossed-cylinder lens and the distance of the lens in front of the cornea. The preferred angle is given by the equation $$\phi = 2 \arctan\left(\frac{1+dD}{1-dD}\right)$$

where $d$ is the distance from cornea to test lens in meters $D$ is the power of each element of the test lens, one positive, one negative, in reciprocal meters (diopters).

The diopter powers for the cylinder lens elements are preferred to be each of about 5 reciprocal meters which value is substituted for the D in the above equation. With this power of crossed-cylinder lens, defects have been observable in about 75 percent of the eyes tested. It is not apparent that the remainder of apparently normal eyes would have any systematic error stable from day to day which could be or should be corrected. However, it would be possible to repeat the test for those eyes using a lens of lesser correction, such as ± 1 or ± 2 diopters. This lens would be more sensitive both to errors in the prescription and to aberrations. Similarly, a more powerful lens would measure eyes having more severe aberrations. The operable range is from about ± 1 diopter to as much as ± 20 diopters. To conduct a test, the trail frame is fitted to the subject, one eye occluded. The test lens is placed in the front slot for the other eye.

Frequently a subject in need of the test already wears glasses; and a lens or lenses are inserted in accord with the subject's eye-glass prescription together with a positive lens correction to account for the nearness of the point source of light. The subject is then asked to view the point source and to describe the center square of the observed pattern. It should be an erect square; but if not, the refraction is adjusted with simple lenses to render it square and erect. The subject is then asked to sketch the whole pattern as observed. In the alternative he may be asked to select from a book of sample pictures, the picture or pictures which show in type and amount the distortion observed.

The test is very sensitive. Some deviation from the ideal square pattern, as indicated by FIG. 3A, has been reported by nearly all subjects tested; moreover, a very wide range of complex defects have been observed, each with its characteristic observed pattern. Using a digital computer, it is possible to generate the power series which describes to any desired degree of approximation the departure from the ideal corneal shape which would produce the observed pattern. One potential value of the test is to determine whether the defect is of a kind which could be helped with contact lenses. At the present time it is not practical to stabilize contact lenses against rotation around the line of sight. Thus, they may be used to correct spherical aberration which results in a pattern as shown in FIG. 3B. This invention provided an impetus for the invention of means for maintaining the rotational orientation of contact lenses.

It will be understood that the present invention is in the nature of a new use for apparatus previously known and an article of manufacture specially adapted to make the new use more simple and practical. Accordingly, it will be understood that the new use may be performed with old apparatus, but it will be further understood that as old apparatus is modified to perform the new use, there will be a point wherein the modified test lens itself will be seen to fall within the scope of the present invention, although it may differ in some respects from the preferred embodiment as herein shown and described. Accordingly, it will be understood that the preferred embodiment and best mode set forth above are merely exemplary, and that the invention is limited by the claims.

We wish to make clear that our characterization of the power of a crossed cylinder lens of ± 5 diopters corresponds to a lens which would have an optician's prescription of − 5 diopters (sphere), + 10 diopters (cylinder). Similarly, a crossed cylinder lens having a power of ± N diopters would have an equivalent optician's prescription of − N diopters (sphere) and + 2N diopters (cylinder).

While there are many ways to build the astigmator with ± 5 diopter power, I prefer to fabricate it from two elements as described above, with a plano-convex cylinder lens 21 and a plano-concave cylinder element 24. The grid is formed using the techniques of the printed-circuit art photochemically deposited directly on one of the plane surfaces. The second plane surface is then cemented over the grid, sandwiching it between the two lens elements. The elements are preferably round, and their edges are protected, and the assembly further held together by the ring 25 which has a groove to engage the edges, bevelled in the usual manner.

I claim:

1. As a new use for the combination of
    I. an article of manufacture comprising
        a. an astigmator lens,
        b. a grid made up of two sets of substantially parallel occluding lines with the lines of each set spaced each from the next by a distance of from ¼ mm. to 2 millimeters, the lines of one of said sets intersecting the lines of the other set at an angle of between 65° and 115°, and
        c. mounting means to hold said grid in a plane parallel to the axes of principal curvature of said astigmator, in close association with said astigmator and with the longer and the shorter diagonals of the cells of said grid parallel respectively to the sections through said astigmator for greatest positive and negative power,
    II. together with means for holding said article as a test eyeglass in front of the eye of a human subject, and
    III. A light source substantially a monochromatic point source, the method comprising the steps of
        1. viewing by the subject said point source through said test eyeglass to see a blurred grid pattern,
        2. optically adjusting the apparatus until the subject observes a predetermined normal pattern for the central cell of said blurred pattern, 3. representing by the subject the appearance of the whole visible blur pattern as a diagram, and
4. determining the amount and kind of aberration by comparison of said diagram with standard diagrams representative of known aberrations.

2. The method of claim one wherein said combination includes a set of lenses of various powers, and wherein said supporting means are adapted to hold selected ones from said set in optical alighment with said eyeglass, and wherein said adjusting step is carried out by inserting selected ones of said lenses into said supporting means.

3. The method of claim one wherein said subject represents said appearance by drawing the observed pattern with a writing instrument.

4. The method of claim one wherein said representing step is accomplished by selecting a pattern from a prerecorded set of illustrations.

5. The method of claim one wherein said representing is accomplished by adjusting the controls of a computer console to generate a matching pattern.

6. The new use as defined by claim one wherein if said angle is related to the strength of said astigmator and the distance at which said means for holding supports said article from said eye by the equation:

$$\phi = 2 \arctan \left( \frac{1 + dD}{1 - dD} \right)$$

where $\phi$ is said angle, $d$ is the distance from said eye to said article in meters, and $D$ is the power of each of two cylinder-lens elements, one positive, and one negative equivalent to said astigmator.

7. An ophthalmic test lens comprising:
I. an astigmator lens having substantially equal positive and negative powers of between one and twenty diopters,
II. a grid made up of two sets of substantially parallel occluding lines with the lines of each set spaced each from the next by a distance of from ¼ mm. to 2 millimeters; the lines of one of said sets intersecting the lines of the other set at an angle between 65° and 87°, and
III. mounting means to hold said grid in a plane parallel to the axes of principal curvature of said astigmator, in close association with said astigmator and with the longer and the shorter diagonals of the cells of said grid parallel respectively to the sections through said astigmator for greatest positive and negative power.

8. A test lens as defined by claim 5
IV. wherein said astigmator comprises a plano-concave lens element and a plano-convex element of equal and opposite powers, said grid is photochemically deposited on the plane surface of one of said elements, and wherein said mounting means comprises cement to fasten plane surface to plane surface with said grid sandwiched between.

9. A test lens as defined by claim 7
V. wherein said mounting means comprise a metal ring to engage and retain the outer edges of said elements.

10. A test lens as defined by claim 5
IV. wherein said grid is formed of occluding lines deposited on a surface of an element of said astigmator.

* * * * *